(12) United States Patent
Ohanyan (10) Patent No.: US 10,695,515 B2
(45) Date of Patent: Jun. 30, 2020

(54) RODENT INTUBATION SYSTEM

(71) Applicant: Vahagn Ohanyan, Hudson, OH (US)

(72) Inventor: Vahagn Ohanyan, Hudson, OH (US)

( * ) Notice: Subject to any disclaimer, the term of this patent is extended or adjusted under 35 U.S.C. 154(b) by 0 days.

(21) Appl. No.: 16/030,822

(22) Filed: Jul. 9, 2018

(65) Prior Publication Data

US 2019/0009043 A1 Jan. 10, 2019

Related U.S. Application Data

(60) Provisional application No. 62/529,993, filed on Jul. 7, 2017.

(51) Int. Cl.
| | | |
|---|---|---|
| *A61B 1/06* | (2006.01) | |
| *A61M 16/04* | (2006.01) | |
| *A61B 1/07* | (2006.01) | |
| *A61B 1/00* | (2006.01) | |
| *A61B 1/267* | (2006.01) | |
| *A61M 16/10* | (2006.01) | |
| *A61M 39/06* | (2006.01) | |
| *A61M 16/08* | (2006.01) | |

(52) U.S. Cl.
CPC ..... *A61M 16/0472* (2013.01); *A61B 1/00188* (2013.01); *A61B 1/07* (2013.01); *A61B 1/267* (2013.01); *A61M 16/0463* (2013.01); *A61M 16/0488* (2013.01); *A61B 2503/40* (2013.01); *A61B 2503/42* (2013.01); *A61M 16/0833* (2014.02); *A61M 16/104* (2013.01); *A61M 2039/062* (2013.01); *A61M 2039/0626* (2013.01); *A61M 2205/075* (2013.01); *A61M 2205/585* (2013.01); *A61M 2205/6081* (2013.01); *A61M 2250/00* (2013.01)

(58) Field of Classification Search
CPC combination set(s) only.
See application file for complete search history.

(56) References Cited

U.S. PATENT DOCUMENTS

2003/0225313 A1* 12/2003 Borodulin ............ A61B 1/303
600/135

OTHER PUBLICATIONS

Biolite Intubation System, sold at least as early as Jul. 7, 2016, Braintree Scientific, Inc., Braintree, MA, USA, www.braintreesci.com.
Kent Scientific Mouse Intubation Kit, sold at least as early as Jul. 7, 2016, Kent Scientific Corporation, Torrington, CT, USA, www.kentscientific.com.

* cited by examiner

*Primary Examiner* — Sameh R Boles (57) ABSTRACT

A rodent intubation system includes a main body member including a first port, a second port and a third port. The main body member further includes a magnification lens of approximately 3 to 7× magnification power, which lens is rotatably connected to the main body member so that an animal being intubated may be viewed through the magnification lens during use of the system. An intubation catheter is releasably connected to one port. An inflation bulb is removably connected to another port. Yet another port of the three port system is sized and dimensioned to receive a fiber optic cable there through.

12 Claims, 7 Drawing Sheets

RODENT INTUBATION SYSTEM

CROSS REFERENCE TO RELATED APPLICATION

This application claims priority from U.S. Provisional Application No. 62/529,993 filed Jul. 7, 2017, the entirety of which is incorporated herein by reference.

FIELD

The present application relates generally to an intubation system, and more particularly, to a hand operated intubation system for use in connection with surgical procedures for rodents such as mice and rats.

BACKGROUND

In order to conduct a variety of medical research, it is necessary to perform small animal surgical procedures. To perform open chest experiments and surgical procedures in rodents, for example, rats and mice, researchers need to intubate the animal. Because of the difficulty with intubation, many research groups use a surgical approach, tracheostomy. This method is not desirable for chronic and survival surgeries, because of increased risk for infection, inflammation, narrowing of the trachea (postsurgical) and bronchial secretions, which all may lead to respiratory failure.

A second method used by researchers is exposure of the trachea (by making a skin incision and dissecting salivary glands). For survival surgeries this is also not desirable because of increased risk of damaging the glottis and vocal cords, insertion into the wrong location (if inserted into the esophagus the animal will die), and increased chance of infection due to the skin incision.

Several years ago, fiber optic light technology came to be used in research experiments and many labs are using fiber optic wires as a light source for intubation procedures. The advantages and disadvantages of this prior art technique are:

Advantages:

1. The outer diameter of the fiber optic wire is small (0.4-1 mm) which allows the fiber wire to be inserted into the angio-catheter for easy use.

2. By using an adjustable light source, the light intensity may be adjusted.

Disadvantages:

1. The prior art technique requires many hours of practice and assistance.

2. The position of the esophagus is very close to the trachea, so it is easy to go into the trachea, which may harm the animal.

3. The glottis and vocal cords are very small and it is difficult to visualize the organs during a procedure without magnification (the current approach does not use magnification).

4. After intubation, it is necessary to remove the catheter and check the position of the catheter. This takes time and if it is not correct, the animal may be sacrificed.

5. For this prior art intubation technique researchers need to use drugs such as Ketamine/Xylazine (or a similar long-acting anesthetic) for a sufficient period of time to perform the tracheal cannulation. These anesthetics depress respiration and can cause death in the animals; especially in older animals and in those with cardiovascular risk factors.

Given the disadvantages of prior art systems, a safer, easier and faster system for performing rodent intubation procedures is needed.

SUMMARY OF THE INVENTION

A new system for rodent intubation is provided for use in research laboratories which require animal intubation, or where animals have to be intubated involving survival or non-survival surgery experiments which require positive pressure ventilation, such as cardiovascular and pulmonary research labs. This intubation system is useful for all researchers who need to intubate mice and rats for open-chest surgical procedures. Using this system is easy to learn and perform an intubation, requires less practice time, and enables researchers to be successful after practicing on 2-3 rodents.

The present rodent intubation system comprises a main body member including a first port, a second port and a third port. The main body member further includes a magnification lens of approximately 3 to 7× magnification power, which lens is connected to the main body member so that an animal being intubated may be viewed through the magnification lens during use of the system. An intubation catheter is releasably connected to the second port. An inflation bulb is removably connected to the third port. The first port is sized and dimensioned to receive a fiber optic cable there through.

The main body member of the system includes a first lumen extending between the first and second ports, and a second lumen that extends from the second port into fluid or air communication with the first lumen. The magnification lens extends radially away from the main body member at an angle relative to the main body member. The angle of the magnification lens with respect to the main body member is generally from about 70 degrees to about 89 degrees, and preferably about 80 to 85 degrees, which angle enables the focal point of the magnification lens to be aimed at the intubation catheter for optimal viewing. Additionally, the location or position of the magnification lens along the main body member is also provided at a distance to enable optimal viewing of the animal being intubated during use of the system. The magnification lens extends away from the main body member in a direction opposite the second port and inflation bulb.

The main body member also includes an internal seal within the first port, which is configured to prevent unwanted movement of the fiber optic cable during intubation. In addition, the intubation catheter is provided with a mating attachment to enable removable attachment with the second port, so that application of a torque to a proximal end of the intubation catheter causes the intubation catheter to rotate and release from the first port of the main body member.

Using the new intubation system of this application, researchers are able to intubate animals in several seconds. It is unnecessary to anesthetize animals using a systemic anesthetic, and an additional surgical procedure is not needed. The present intubation system provides an easier system to use, which enables faster and safer intubation procedures to be performed by researchers.

DETAILED DESCRIPTION

The present application is for a rodent intubation system having a variety of advantages over current procedures and devices used for intubation.

Figure 1:
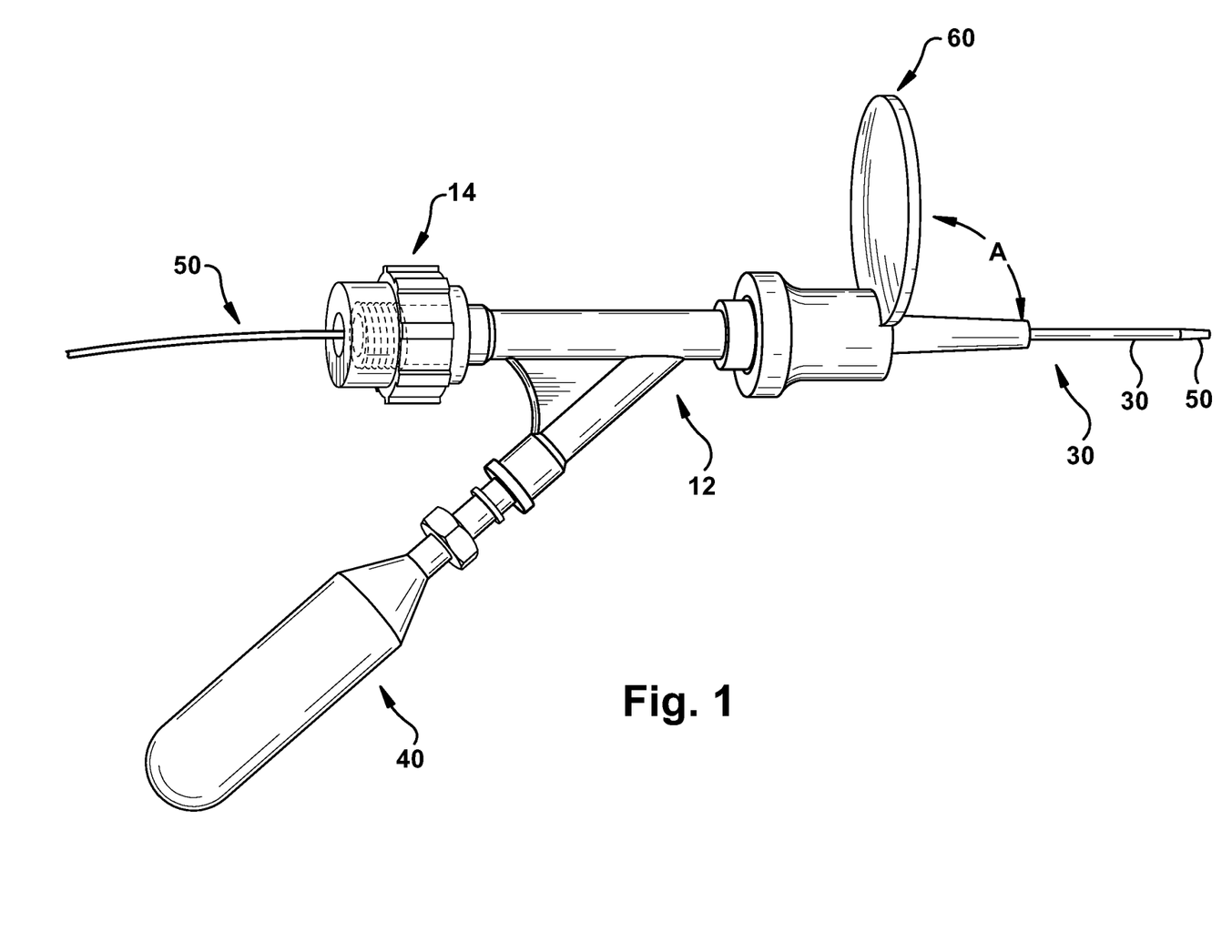
FIG. 1 shows a perspective view of the new rodent intubation system of this application.
Figure 2:
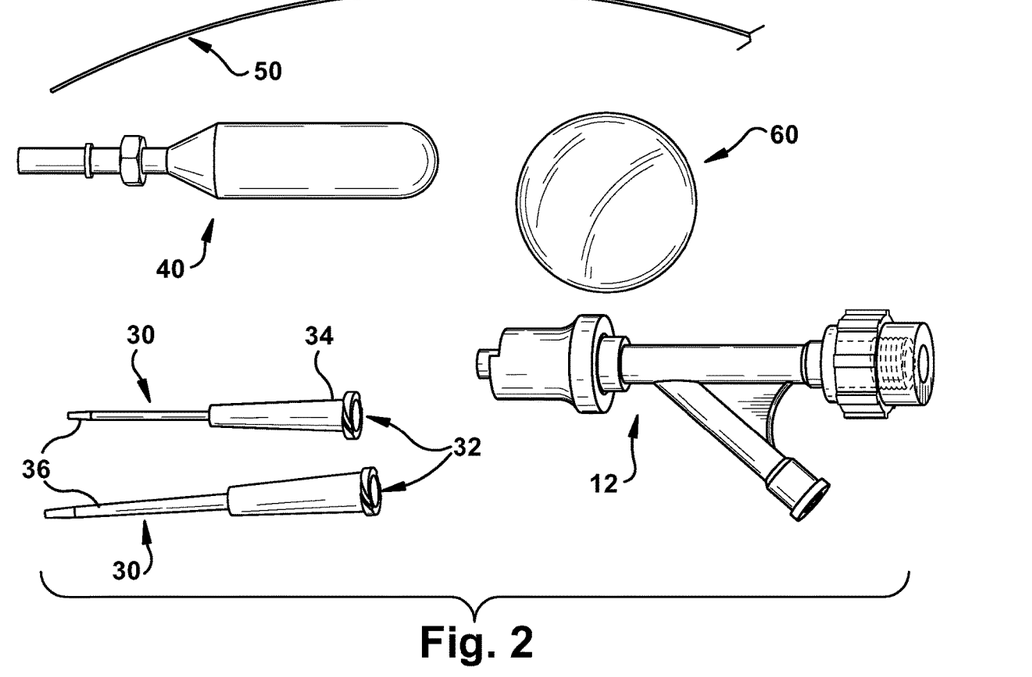
FIG. 2 shows an exploded view of the components of the rodent intubation system of this application.
Figure 3:
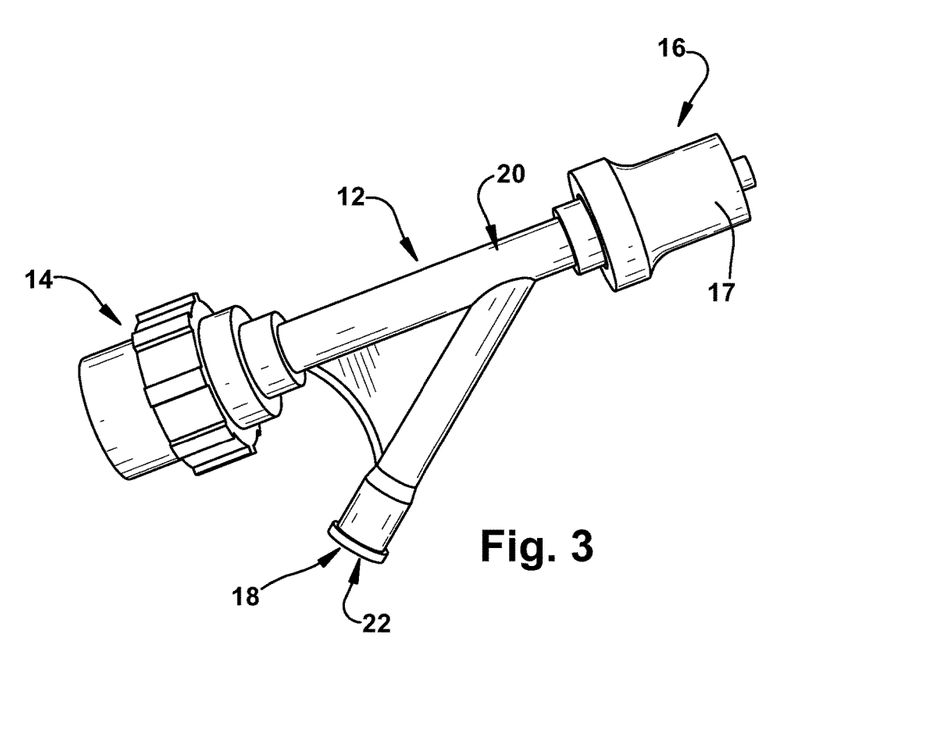
FIG. 3 shows the Y shaped main body member of the rodent intubation system.
Figure 4:
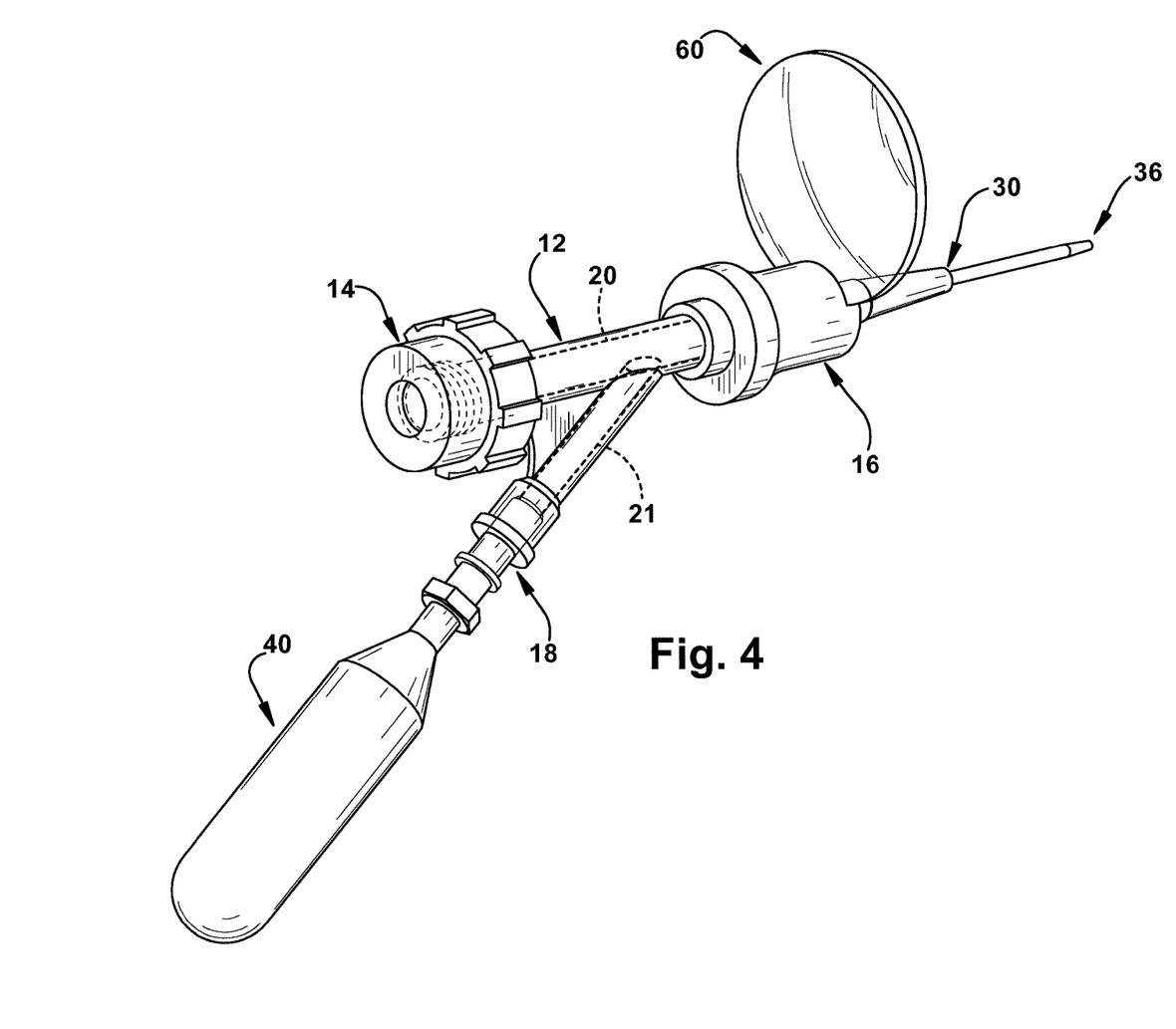
FIGS. 4-6 illustrate schematic, stylized views of the device from an upper side perspective view, side view and perspective rear view, respectively.
Figure 5:
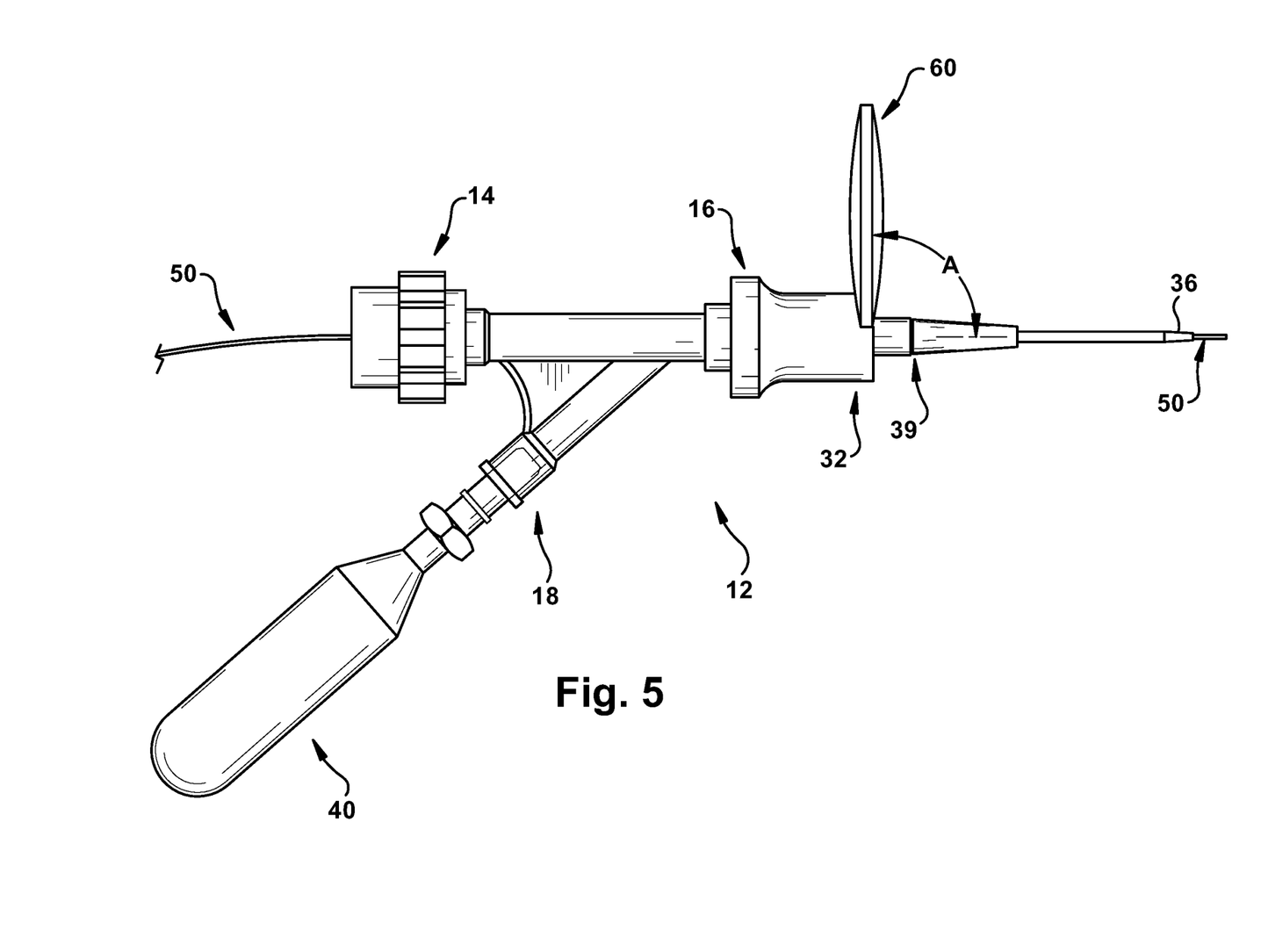
Figure 6:
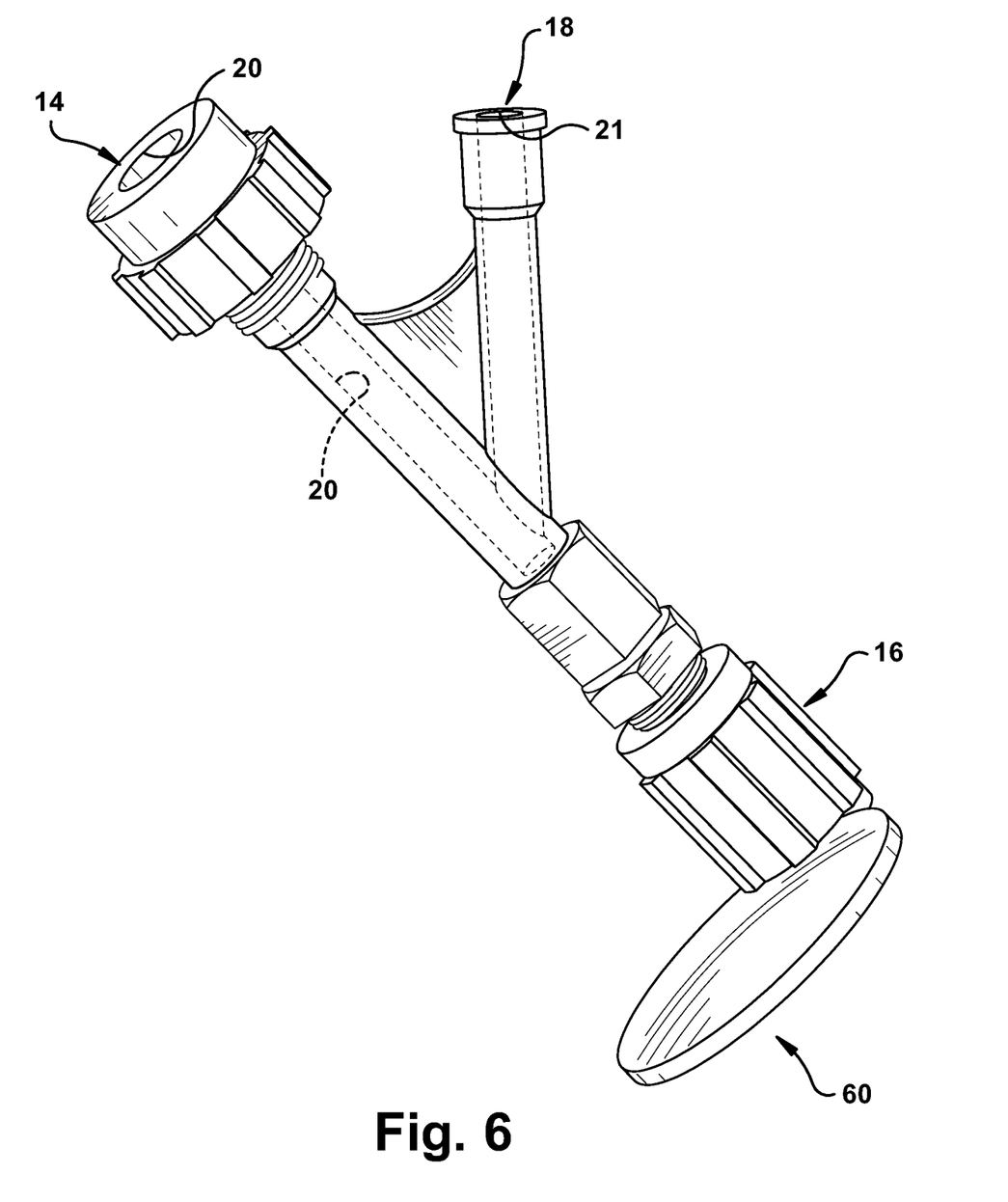

FIGS. 1 to 9 illustrate the rodent intubation system 10 of this application. The system components are shown in FIG. 2, and are illustrated at least including:

A valve 12, which is a conventional hemostasis valve, or a Y shaped main body member, as shown in FIG. 3, having at least three ports;

An intubation angio-catheter 30, where the size of catheter used ranges from 15-22 G (gauge), with a proximal end for removable attachment to a port on the main body member;

A flexible polymer inflation bulb 40, removably attached to a port of the main body member;

A fiber optic light wire 50, having a size ranging from 0.4-2 mm, but preferably 0.4-1 mm engaged into one port of the main body member and out through a second port; and A polymer magnification lens 60, having a magnification strength of from 3-7× power.

Figure 9:
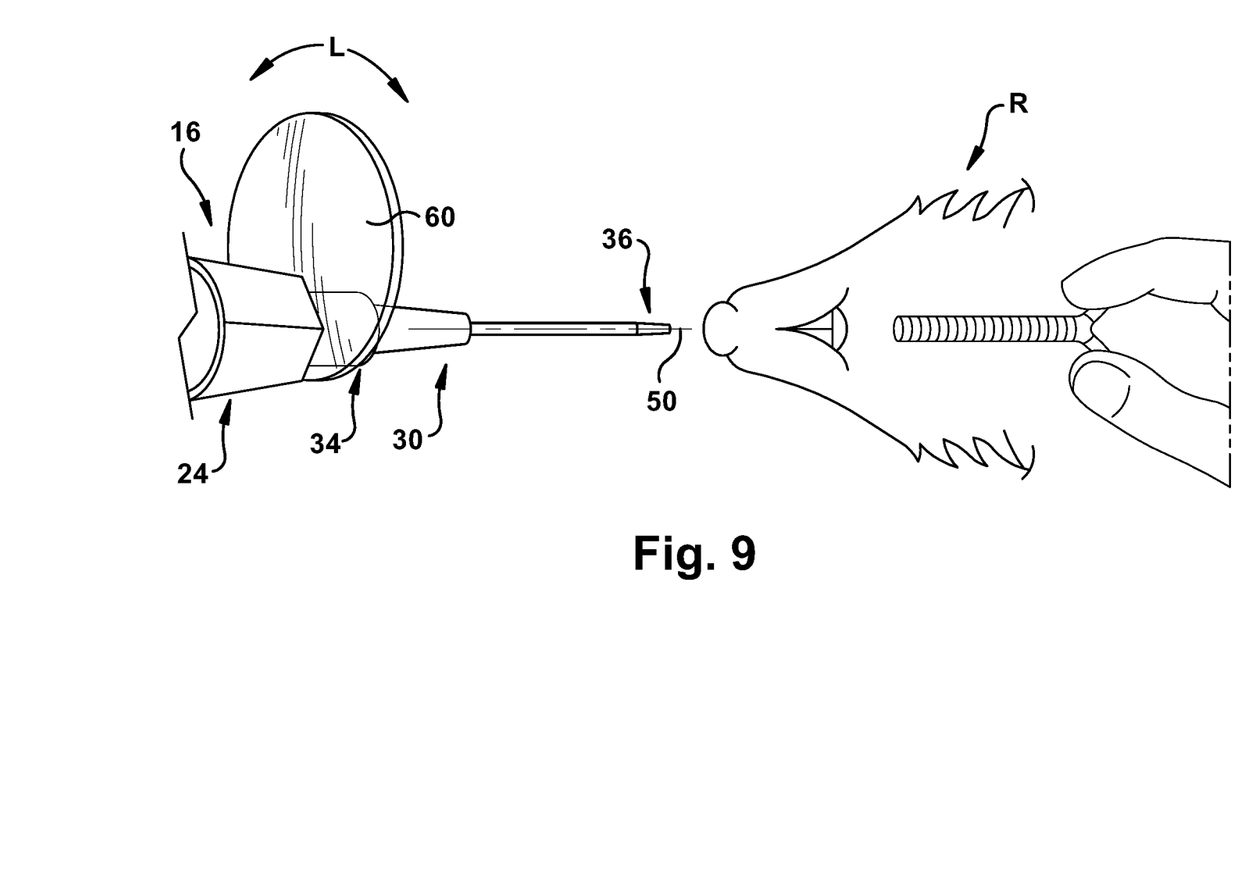
FIG. 9 schematically illustrates a rodent positioned for intubation using the rodent intubation system of this application.

In order to see the glottis, vocal cords and trachea of the rodent clearly (as schematically illustrated in FIG. 9), the system components are assembled into one device (a single unit) to provide the user with a magnified view of the animal, which makes the intubation procedure easier and faster. The new intubation system of this application has at least the following advantages:

A) Single-handed manual operation.

B) Small size.

C) The inflation bulb 40 is removably connected to a lower port 18 of the three port system, so it is easy to check the position of the catheter 30—since by squeezing the manually operated bulb, the rodents lungs can be seen to expand. Also there is no need to disconnect the catheter 30 from the system 10 to check the catheter position.

D) The system 10 is adjustable for the use of different sized fiber optic wires 50, depending on rodent size.

E) An important component of the system is the magnification lens 60 or loop, preferably having a 3-7× magnification strength. This feature allows the user clearly to visualize the vocal cords, glottis and all anatomical structures needed for performing a proper intubation procedure. The magnification lens 60 is rotatable a full 360 degrees to view the adjacent intubation catheter 30 from any desired angle, for ease of adjustment and use by both right and left handed researchers.

F) The intubation system 10 of this application does not require systemic Ketamine/Xylazine anesthesia to be administered to the rodent during use. Instead, by using the intubation system with only Isoflurane administered, the animals can be intubated for less time, or from 10-30 seconds. This enables a safer procedure for the animals.

G) The use of a rotatable connector attachment 17 between a second port 16 of the Y shaped main body member and the intubation catheter 30, enables easy removal of the catheter from the second port 16 of the main body member 12 after successful intubation.

H) The system of this application provides a safe, easy and fast intubation procedure for rodents.

The rodent intubation system 10 of this application is a novel intubation system not currently available in the market. While several companies sell fiber optic wire, such devices do not have magnification or attached magnification lenses, nor do they have magnification combined with an inflation bulb to test whether or not intubation is successful. For example, a fiber optic light wire available in the market as the Biolite system, for example at www.braintreesci.com. This prior art device is a fiber optic wire connected to light source. Kent Scientific provides a similar prior art kit product available from www.kentscientific.com. Available systems also fail to provide an interconnected inflation bulb and there is no magnification ability or loop.

The problems encountered when using these currently available devices, and the failure to provide a tool or system for easy and efficient performance of a rodent intubation procedure, are solved by the rodent intubation system 10 of this application. The present system is:

A) Safer for the animal being intubated, since less anesthesia is required and surgery can be shorter, resulting in a higher success rate.

B) Easy to operate, so the intubation procedures performed can be conducted faster and with less practice.

C) Less expensive to manufacture and to purchase.

Again, the use of an intubation system of this application provides the following advantages over prior systems:

The present system facilitates single-handed operation by the user. The system is small in size, measured at between 11 and 13 cm, preferably 12 cm, from the end of the installed inflation bulb 40 to the magnification lens 60.

The main body member 12, which is a conventional Y-shaped hemostasis valve, is of the type available, for example, from Medline Industries, Inc., www.medline.com. The main body member 12 has a seal end or port 14 (blue colored in commercial products, or located at the top and rear of the valve 12 during use) which provides security that the fiber optic wire 50 will stay in place during use, and will enable easy adjustment of the wire length. This first port 14 is sized to allow insertion of up to 2 mm diameter fiber optic wires, however, for example, for a 6 to 15 mg mouse, a fiber optic wire with an outer diameter (OD) of 0.4 to 0.55 mm, would be used. For a 15 to 60 mg mouse, a fiber optic wire with an OD of 0.55 to 0.65 mm would be used. For a rat, a fiber optic wire with an OD of 0.7 to 1 mm may be appropriate, with up to a 2 mm outer diameter available if needed for a larger animal.

The second end or port 16 (red colored in commercial products, or located at the top and front of the valve 12 during use) of the main body member 12 includes a fully rotatable connector attachment 24 with an internally threaded end 17 for mating engagement with mating structure 32 provided on the intubation angio-catheter 30. This port attachment 17 allows easy attachment and removal of the intubation angio-catheter 30 from the connector attachment 24 secured to the main body member 12. The size of the intubation angio-catheter 30 attached, at a proximal end 34 having the mating structure 32 engaged with the second port 16 may, for example, for a 6 to 15 mg mouse be in the range of 21-22 G. For a 15 to 60 mg mouse, an intubation angio-catheter of 20 G would be used. For a rat, an intubation angio-catheter of 15-16 G would be used. As shown in FIGS. 1 and 9, during use, the fiber optic wire 50 is positioned to illuminate the rodent organs, and extends from a conventional light source (not shown) through the first port 14, through a first lumen 20 of the valve 12, which connects the first and second ports 14, 16, and out a distal end 36 of the intubation angio-catheter 30 secured to the second port 16 to illuminate the rodent for intubation.

The third port, open end or port 18, of the hemostasis valve 12, located at the bottom and rear of the valve during use, or spaced from and below the first seal port 14, enables connection of a removable inflation bulb 40, for example, by threaded or press fit engagement. After intubation and removal of the light wire, the position of the distal end 36 of the catheter 30 may be checked. By squeezing the flexible polymer inflation bulb 40, to manually inflate and deflate the flexible inflation bulb, the researcher may visually confirm by the rise and fall of the rodent chest (lungs) that the catheter is properly positioned. Thus, the catheter 30 need not be removed or taken out of the system to check the position of the intubation catheter.

The properly angled and located magnified optic polymer lens 60, which is secured to the rotatable connector attachment 24 of the main body member 12 adjacent the second port 16, allows clear visualization of the rodent anatomical structures to enable successful intubation of the animal. As shown in FIG. 1, the angle A at which the lens 60 is secured in position, as measured from near the proximal end 34 of the intubation catheter 30, is in the range of 89 to 75 degrees, or less than 90 degrees. The lens 60 is secured to the rotatable connector attachment 24 on a side of the main body member 12 opposite the third port 18 and inflation bulb 40. The ability of the lens 60 to rotate 360 degrees around the intubation catheter, in the direction of the arrow L shown in FIG. 9, enables viewing of the animal R from any desired angle. As a result, the device 10 is able to be used by either right handed or left handed researchers, as the lens may be moved to any convenient angle for visualizing the animal.

Figure 7:
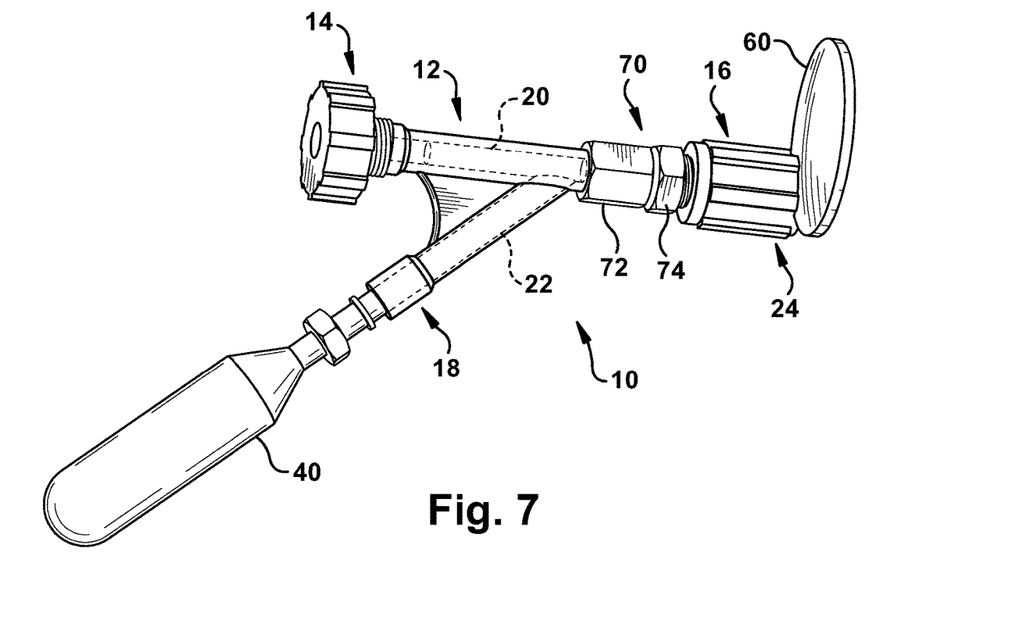
FIG. 7 shows side perspective view of an alternate embodiment of the new rodent intubation system having a threaded connector positioned intermediate the Y shaped main body member and the second port and magnification lens.
Figure 8:
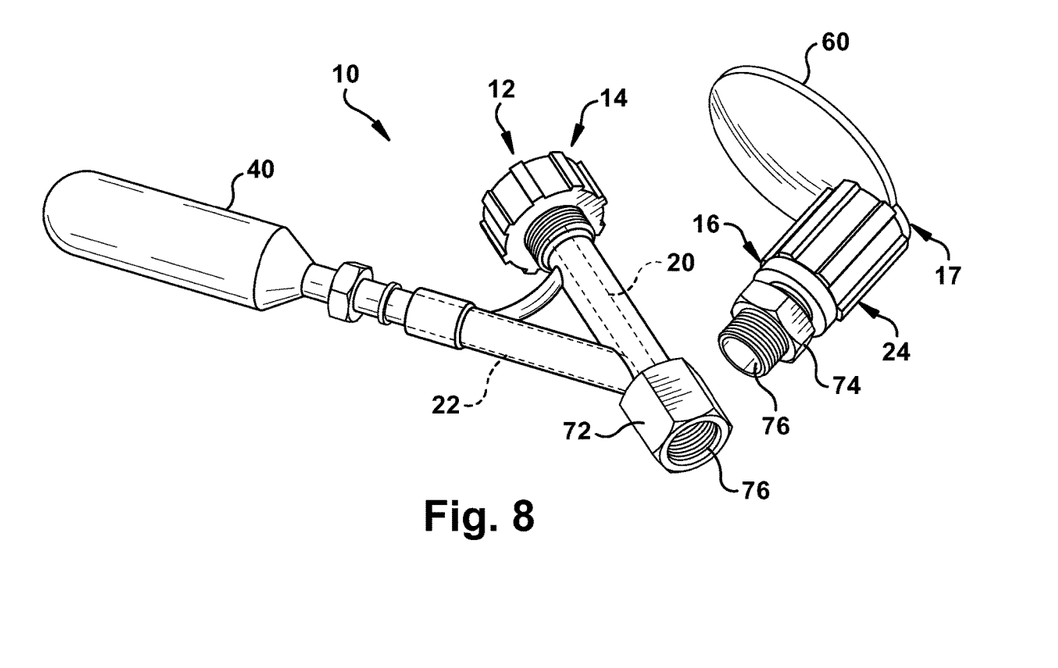
FIG. 8 shows a side perspective view of the embodiment of FIG. 7, with the Y shaped main body member and the second port and magnification lens disconnected at the threaded connector.

In the alternate embodiment shown in FIGS. 7 and 8, a two-piece male-female threaded connector 70 is provided as an additional component. The connector 70, preferably of medical grade stainless steel, is positioned with a female end 72 engaged in communication with the first lumen 20, and a male end 74 secured to the rotatable connector attachment 24 and second port 16. A central opening 76 through both portions of the connector 70 is sized to enable the light wire 50 to pass from the first port 14 to the intubation catheter 30. By using connector 70 at the location indicated, the attached magnification lens 60 may be removed and replaced, together with the connector attachment 24, in the event the lens becomes scratched or blurry after multiple uses and sterilizations.

Use of the system enables rodents to be intubated very quickly, or within 10-20 seconds. Once the intubation catheter 30 is properly placed, the animal R may be connected to a ventilator system, which provides both anesthesia and oxygen via the catheter.

A method for intubating a rodent is disclosed using the system described which DOES NOT require intubation surgery or the use or administration of a Ketamine/Xylazine anesthesia cocktail to the rodent. Only a gas anesthesia is used. Gas anesthesia has many advantages, such as easy and fast induction of the anesthesia and a shorter recovery period for the animal.

While certain embodiments of the invention have been described with specificity in order to improve understanding of the invention, many variations and modifications will become apparent to a person of ordinary skill in the art. It is therefore expected and intended that the certain changes and modifications may be practiced which will still fall within the scope of the appended claims.

I claim:

1. A rodent intubation system comprising:
a main body member including a first port, a second port and a third port, the main body member further including a magnification lens connected thereto adjacent a port;
an intubation catheter releasably connected to the second port; and
a flexible inflation bulb connected to the third port;
wherein the first port is sized and dimensioned to receive and seal a fiber optic cable there through.

2. The system of claim 1, wherein the main body member includes a first lumen, having a central axis, and the first lumen extends between the first and second ports, and a second lumen that extends from the third port into atmospheric communication with the first lumen.

3. The system of claim 2, wherein the magnification lens is rotatable about the central axis of the first lumen for adjustment of the magnification lens location with respect to the adjacent port.

4. The system of claim 2, further comprising a two-piece male-female connector having a central opening, the connector positioned intermediate the first lumen and the second port.

5. The system of claim 4, wherein the first port of the main body member further includes an internal seal configured to prevent unwanted movement of the fiber optic cable during intubation.

6. The system of claim 1, wherein the magnification lens extends radially away from the main body member at an angle relative to the main body member.

7. The system of claim 6, wherein the magnification lens is at an angle with respect to the main body of about 70 degrees to about 89 degrees, in a direction toward the intubation tube catheter.

8. The system of claim 1, wherein the first port of the main body member further includes an internal seal configured to prevent unwanted movement of the fiber optic cable during intubation.

9. The system of claim 1, wherein the intubation catheter includes a mating attachment at a proximal end for engagement with the second port so that application of a torque to a proximal end of the intubation catheter causes the intubation catheter to rotate and release from the main body member.

10. The system of claim 1, wherein the magnification lens is configured to provide a magnification power of about 3-7×.

11. A rodent intubation system comprising:
a main body member including a first port, a second port and a third port, the main body member further including a magnification lens of 3-7× connected for rotation with respect to the main body member at a position adjacent the second port, and the magnification lens extends radially away from the main body member at an angle relative to the main body member of less than 90 degrees;

an intubation catheter releasably connected to the second port;

a flexible inflation bulb connected to the third port; and the first port, main body member, second port and intubation catheter are sized and dimensioned to receive a fiber optic cable there through.

12. The system of claim 11, wherein the main body member includes a first lumen, having a central axis, and the first lumen extends between the first and second ports, and a second lumen that extends from the third port into atmospheric communication with the first lumen and the intubation catheter.

* * * * *